(12) United States Patent
Miner

(10) Patent No.: US 6,649,181 B1
(45) Date of Patent: Nov. 18, 2003

(54) COSMETIC ADHESIVE STRIP

(75) Inventor: Philip Edward Miner, Newtown, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/156,870

(22) Filed: May 29, 2002

(51) Int. Cl.[7] ................ A01N 25/34; A61F 16/00; A61K 9/70
(52) U.S. Cl. ................ 424/402; 424/401; 424/443
(58) Field of Search .............. 424/78.03, 401, 424/402, 443

(56) References Cited

U.S. PATENT DOCUMENTS

| | | |
|---|---|---|
| 766,963 A | 8/1904 | Murray |
| 1,291,846 A | 1/1919 | Greenfield |
| 2,001,862 A | 5/1935 | Battey |
| 2,438,771 A | 3/1948 | Topjian |
| 4,631,227 A | 12/1986 | Nakamura |
| 4,719,909 A | 1/1988 | Micchia et al. |
| 4,745,916 A | 5/1988 | Seber |
| 5,512,277 A | 4/1996 | Uemura et al. |
| D388,533 S | 12/1997 | Uemura et al. |
| D388,534 S | 12/1997 | Uemura et al. |
| 6,042,844 A | 3/2000 | Ishida et al. |
| 6,106,818 A | 8/2000 | Dulog et al. |
| 6,221,382 B1 | 4/2001 | Ishida et al. |
| 6,261,593 B1 * | 7/2001 | Muchin et al. ............ 424/443 |
| 6,299,605 B1 | 10/2001 | Ishida |
| 6,306,382 B1 | 10/2001 | Uemura et al. |

FOREIGN PATENT DOCUMENTS

| | | | |
|---|---|---|---|
| JP | 60-165902 | 8/1985 | |
| JP | 61-23916 | 2/1986 | |
| JP | 6-4032 | 1/1994 | |
| JP | 06/4032 | * 1/1994 | ............ A61K/7/48 |
| JP | 8-011906 | 1/1996 | |
| JP | 8-269809 | 10/1996 | |
| WO | 97/32597 | 9/1997 | |

OTHER PUBLICATIONS

Pond's clear pore strips packaging 1997.*
Copy of Pond's Clear Pore Strips Packaging Box—1997.

* cited by examiner

Primary Examiner—Thurman K. Page
Assistant Examiner—Micah-Paul Young
(74) Attorney, Agent, or Firm—Milton L. Honig

(57) ABSTRACT

An adhesive strip, particularly for application to the nose, is provided which includes a holding member layer and deposited thereon a cosmetic material layer. Structurally the strip includes an upper edge and lower edge. A centrally located receding portion is featured along the upper edge and is flanked on either side by a continuously curving wing portion extending to a respective side edge of the strip. Along the lower edge is a centrally located downwardly projecting portion flanked on each side by downwardly sloping wing portions. The shape is designed to avoid discomfort associated with known strips when they are peeled away from the membrane areas immediately below the eye.

4 Claims, 1 Drawing Sheet

COSMETIC ADHESIVE STRIP

BACKGROUND OF THE INVENTION

1. Field of the Invention

The invention relates to an adhesive cosmetic strip of special geometry and use of that strip in a method for removing keratotic plugs from skin pores, especially those along the nose.

2. The Related Art

Highly visual pores on facial skin surfaces are perceived, especially by women, to be a serious beauty problem. The conspicuous nature of this problem is caused by keratotic plugs formed within pores of the skin. Keratotic plugs are dead epidermal cells keratinized together with sebaceous matter and dirt. Absent proper treatment, not only will beauty suffer but also various dermatological problems may arise. Removal with detergents or with make-up removers (e.g. cold cream) have not provided adequate solution to the problem. Squeezing the skin in an attempt to remove keratotic plugs can lead to infections which can damage skin.

U.S. Pat. No. 5,512,277 and U.S. Pat. No. 6,306,382, both to Uemura et al., report a keratotic plug remover composition based upon a peelable mask formed from a resin functionalized with salt forming groups. The resin is applied in a wet state onto the skin. While still fluid, the resin flows into the pores. Water is allowed to evaporate from the composition causing the resin to harden into a peetable film. Removal of the hardened film simultaneously causes adhered plugs to be removed.

Subsequent elaboration of this technique utilized a water-insoluble non-woven substrate as a carrier for the film-forming cosmetic resin. Improved film integrity and peelability was a major advantage in use of a non-woven substrate.

Illustrative of this technology is U.S. Pat. No. 6,299,605 B1 (Ishida), assigned to the Kao Corporation, and commercially embodied in Biore® Cleansing Pore Strips available in this country in 1997. Early models of the plug removing nose strip from Biore utilized a geometry wherein both upper and lower edges were formed as straight lines parallel to one another. U.S. Pat. No. 6,299,605 B1 illustrates this prior art in FIG. 10 through 13B. An improvement on that geometry is described in the patent. FIGS. 5 and 6 illustrate the improvement by a shape which allows along a tower edge a projecting portion capable of now covering the tip of the nose. As an aid to manufacture, a complementary concave receding portion is formed at the upper edge of the strip. Sheet packs of multiple strips are said to be manufacturable without waste through the complementary fitting of the projecting portion of a first strip into the receding portion of a second.

Pond's® Cleansing Pore Strips followed the Biore® product to market. Another step improvement was achieved by the geometry of the Pond's® strip. Instead of flanking the receding and projecting portions with pairs of adjacent straight linear portions, the latter were replaced with angled downwardly sloping pairs of flanking portions.

Despite the significant progress, there still have been consumer complaints about the pain associated with the peeling step.

Skin membrane directly beneath the eye is relatively tender. Known pore strips placed over the nose ordinarily arrange themselves with wings that adhere to the tender membrane under the eyes.

Considerable pain occurs when those wings are forcibly peeled.

Geometric form can thus be extremely important in the painless removal of strips.

Accordingly, it is an advantage of the present invention to provide a cosmetic adhesive strip capable of extracting keratotic plugs from the nose white minimizing pain in their removal.

SUMMARY OF THE INVENTION

An adhesive strip for the nose is provided which includes:
(i) a holding member layer;
(ii) a cosmetic material layer deposited onto the holding member layer;
  wherein the strip includes an upper edge and a lower edge, the upper edge including a centrally Located receding portion flanked on each side by a continuously curving winged portion extending to a respective side edge of the strip;
  the lower edge including a centrally located downwardly projecting portion flanked on each side by downwardly sloping winged portions.

Respective side edges of the strip connect respective upper and lower edges. Advantageously the respective side edges have a straight non-curved section, preferably along all their respective length. In the preferred embodiment, no other straight sections are present other than the straight non-curved section of the respective side edges.

Another aspect of the preferred embodiment is that the downwardly sloping wing portions terminate in respective rounded corners. These corners are adjacent to the respective side edges.

The projecting portion and each round edge have respective tips at maxima of their curvature. Advantageously, all three tips lie in a common plane that is perpendicular to a major surface of the strip.

Both upper and lower edges are essentially sinusoidal. The upper edge has curvature with one minima and two maxima. This contrasts with the Lower edge having three maxima and two minima.

Strips of the present invention may be limited to a single holding member layer such as a non-woven fabric and to a layer of a cosmetic material. Some embodiments may have more than these two layers. For instance, embodiments where the surface of the strip is stored with an adhesively tacky surface, a backing layer can be applied over the tacky surface. This prevents sticking of one strip to another. Other embodiments may include more than one layer of the holding member. For instance, the holding member may be a combination of separate cellulosic and synthetic fibered plastic layers (e.g. a paper web joining a polyethylene web).

The preferred mode of the present invention is that the strip be impregnated with a cosmetic material that is a composition dry non-tacky to the touch after deposition onto the holding member. Yet upon being wetted for use, the composition turns tacky and mobile thereby providing adhesivity to the holding member against skin.

BRIEF DESCRIPTION OF THE DRAWING

Further advantages and features of the present invention will become more apparent from consideration of the drawing which consists of a sole FIG. 1 which is a top plan view of a best mode strip.

DETAILED DESCRIPTION OF THE INVENTION

Figure 1:
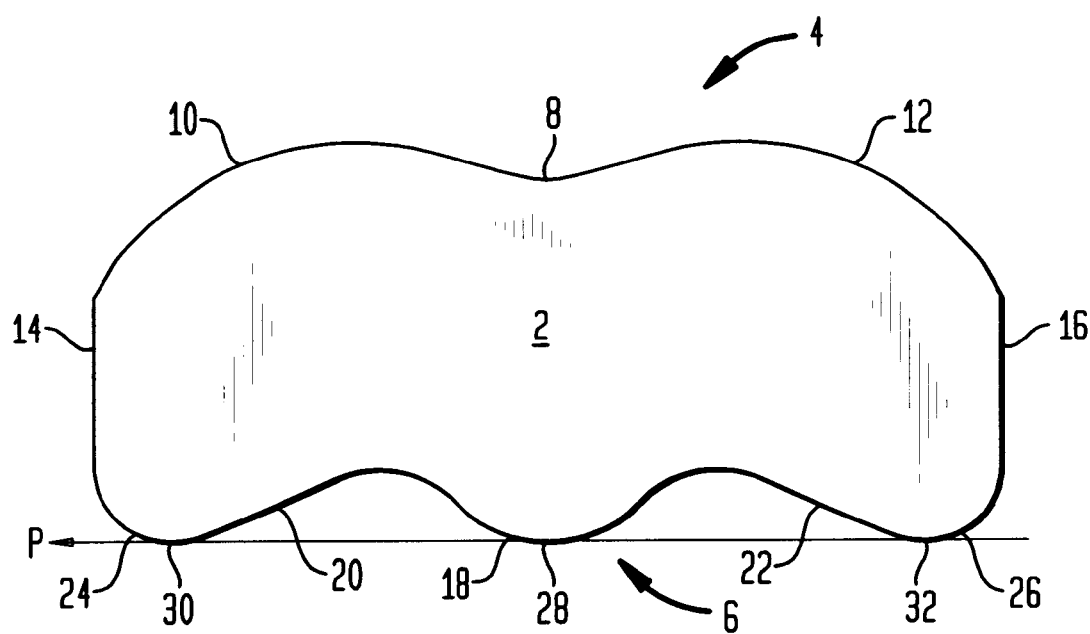

The problem of the present invention has been solved by improving the shape of an adhesive strip meant for application over the nose. A relatively shallow centrally located receding portion is fashioned in an upper edge of the strip. A continuously curving wing portion flanks the receding portion. By the continuous curve of the wing portion, sensitive membrane areas under the eye are to a large extent not contacted by the wing portions. Removal of the improved strip causes less pain in the peeling process.

FIG. 1 illustrates the preferred embodiment. The strip is formed from a holding member layer 2 with a cosmetic material layer deposited onto the holding member layer. Geometrically the strip includes an upper edge 4 and a lower edge 6. The upper edge features a centrally located receding portion 8 flanked on each side by a continuously curving wing portion 10, 12.

Left and right side edges 14, 16 join the upper and lower edges. The continuously curving wing portions extend to the respective side edges.

A centrally located downwardly projecting portion 18 is formed along the lower edge and flanked on each side by downwardly sloping wing portions 20, 22.

The downwardly sloping portions terminate in respective rounded corners 24, 26. These corners are adjacent the respective side edges.

The downwardly projecting portion and the rounded corners each have tips 28, 30, 32 at maxima of their curvature. These tips are aligned along a common plane P. This plane is oriented perpendicular to a major surface (i.e. the holding member layer 2) of the strip.

The holding member in the preferred embodiment is a flexible non-occlusive substrate sheet impregnated with a cosmetic material in the form of an adhesive composition containing an anionic, cationic, nonionic or amphoteric polymer. In a dry state, the composition is non-tacky to the touch. The product is used by either directly wetting the composition on the sheet or indirectly by wetting the face in areas to be contacted by the composition. In either instance, the wetting agent interacts with the composition so it becomes tacky and sufficiently mobile to flow into skin pores. Pure water is the preferred wetting agent. However, other fluid systems or gels could be employed. Suitable fluids would include alcohols such as ethanol, propanol, propylene glycol, polyethylene glycol, polypropylene glycol and especially mixtures of these alcohols with water. Gels would normally consist of fluid (particularly water) and structuring agents such as Carbomer.

Subsequent to wetting the composition is allowed to dry over the area of treatment. During drying the keratotic plugs stickingly adhere to the composition. Advantageously the drying period ranges from 1 minute to 5 hours, preferably from 5 minutes to 1 hour, optimally from 10 to 20 minutes. Thereafter, the dried composition with adhered plugs is peeled from the skin.

Most polymers suitable for the present invention will be relatively brittle when dried. Therefore, they require a supporting surface which is a flexible substrate sheet. Substrate sheets of the present invention must be non-occlusive to allow water evaporation from the deposited polymer as the film maturates. Non-occlusivity or breathability is achieved either through use of a hydrophobic substrate having physical porosity (e.g. pore channels) or a hydrophilic substrate wherein the material of construction inherently allows for breathability. Suitable materials include cellulosics such as rayon, wool, cotton, linen and combinations thereof. They may be woven or nonwoven. Nonwoven rayon is a preferred substrate. Ordinarily hydrophobic substrates are unsuitable. For instance, untreated polyethylene is hydrophilic but hydrophilically treated (e.g. coated) polyethylene may be useful. However, if hydrophobic substances are so constructed with a fiber geometry to allow for breathability, they may also be employed. Under these conditions, polyesters, polyamides, vinyl resins and other thermoplastic fibers could be suitable. Materials formed from combinations of cellulosic with thermoplastic fibers may also be employed subject to breathability. For instance, a hydrophilic polypropylene/rayon combination can be employed for the present invention.

It is advantageous to employ a ratio of composition to substrate (i.e. cosmetic material to holding member layer) in amount ranging from 0.1:1 to 1,000:1, preferably 0.5:1 to 100:1 and optimally 0.8:1 to 10:1 by weight. The polymer ordinarily will constitute from 25 to 100%, preferably from 50 to 95%, optimally from 75 to 85% by weight of the composition deposited onto the substrate sheet.

Minor adjunct ingredients may also be included such as fragrances, skin care additives, opacifiers and colorants, each in their effective amounts to accomplish their respective functions.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

EXAMPLE

A consumer response evaluation was conducted to compare Pond's® Clear Pore Strips, a commercially available product, to the new shape strip of the present invention. The cosmetic material layer deposited onto the holding member layer was identical in both the commercial and experimental strips. Likewise, the material used for the holding member layer was identical. In fact, the only change was in the outer shape of the strip.

Consumers were divided into two groups. One group were current nose strip users who used the Pond's® product and the second did not use this product. There were 6 people in the "do use" group and 8 people in the "do not" use group (the latter utilized Kao Biore® Cleansing Strips). Each person was asked which shape they preferred and why. The results are reported in the Table below.

TABLE

| PRODUCT | PREFER CURRENT SHAPE | PREFER NEW SHAPE |
|---|---|---|
| Pond's ® | 1 to 6 | 5 to 6 |
| Biore ® | 2 to 8 | 6 to 8 |

Among the reasons why the new shape was preferred, the two most mentioned were:
1. The new shape doesn't extend as far into the sensitive under-eye area (both groups mentioned this).
2. The new shape, with its curved edges, were smoother to the touch. The Biore® users particularity mentioned this, as the Biore® shape has two pointed corners.

Evident from the above result is that the new shape provides advantages over the existing shape due to its current edges and improved coverage.

The foregoing description and example illustrates selected embodiments of the present invention. In light thereof variations and modifications will be suggested to one skilled in the art, all of which are within the spirit and purview of this invention.

What is claimed is:

1. An adhesive strip suitable for application to the nose comprising:
   (i) a holding member layer;
   (ii) a cosmetic material layer deposited onto the holding member layer;
      wherein the strip comprises an upper edge and a lower edge, the upper edge comprising a centrally located receding portion flanked on each side by a continuously curving winged portion extending to a respective side edge of the strip;
      the lower edge including a centrally located downwardly projecting portion flanked on each side by downwardly sloping winged portions; the respective side edges connecting the upper to the lower edges, the downwardly sloping wing portions terminating in respective rounded corners, the respective rounded corners being adjacent the respective side edges, the projecting portion and each round corner having respective tips at maxima of their curvature, and all three of the tips lying in a common plane that is perpendicular to a major surface of the strip.

2. The strip according to claim 1 wherein the respective side edges comprise a straight non-curved section.

3. The strip according to claim 3 wherein no other straight sections are present other than the straight non-curved section of the respective side edges.

4. The strip according to claim 1 wherein the cosmetic material layer is dry non-tacky to the touch and upon being wetted for use turns tacky and mobile.

* * * * *